United States Patent
Parthasarathy et al.

(10) Patent No.: US 11,634,666 B2
(45) Date of Patent: Apr. 25, 2023

(54) METHODS FOR SPORE REMOVAL COMPRISING A POLYSORBATE SURFACTANT AND CATIONIC ANTIMICROBIAL MIXTURE

(71) Applicant: 3M INNOVATIVE PROPERTIES COMPANY, Saint Paul, MN (US)

(72) Inventors: Ranjani V. Parthasarathy, Woodbury, MN (US); Catherine D. Heapy, North Saint Paul, MN (US); Tiffany J. Hanson, Woodbury, MN (US); Brittney K. T. Scott, Philadelphia, PA (US); Jonathan D. M. Helander, Riverside, CA (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/063,455

(22) PCT Filed: Dec. 19, 2016

(86) PCT No.: PCT/US2016/067441
§ 371 (c)(1),
(2) Date: Jun. 18, 2018

(87) PCT Pub. No.: WO2017/112567
PCT Pub. Date: Jun. 29, 2017

(65) Prior Publication Data
US 2018/0362895 A1 Dec. 20, 2018

Related U.S. Application Data

(60) Provisional application No. 62/270,701, filed on Dec. 22, 2015.

(51) Int. Cl.
*C11D 3/48* (2006.01)
*A61K 8/84* (2006.01)
*A61K 8/34* (2006.01)
*A61Q 17/00* (2006.01)
*A01N 31/14* (2006.01)
*A01N 47/44* (2006.01)
*C11D 3/20* (2006.01)
*C11D 3/37* (2006.01)
*C11D 11/00* (2006.01)
*C11D 17/04* (2006.01)

(52) U.S. Cl.
CPC ............... *C11D 3/48* (2013.01); *A01N 31/14* (2013.01); *A01N 47/44* (2013.01); *A61K 8/347* (2013.01); *A61K 8/84* (2013.01); *A61Q 17/005* (2013.01); *C11D 3/201* (2013.01); *C11D 3/2034* (2013.01); *C11D 3/2068* (2013.01); *C11D 3/3703* (2013.01); *C11D 11/0011* (2013.01); *C11D 17/041* (2013.01)

(58) Field of Classification Search
CPC ...................................................... C11D 1/667
See application file for complete search history.

(56) References Cited

U.S. PATENT DOCUMENTS

| | | | |
|---|---|---|---|
| 5,084,096 A | 1/1992 | Stovicek | |
| 5,408,022 A | 4/1995 | Imazato | |
| 5,968,852 A * | 10/1999 | Vlasblom | ............... A47K 7/03 428/304.4 |
| 6,164,441 A * | 12/2000 | Guy | ................... B65D 75/5838 206/210 |
| 6,248,343 B1 * | 6/2001 | Jampani | ................. A01N 47/12 424/401 |
| 6,383,505 B1 | 5/2002 | Kaiser | |
| 6,440,405 B1 | 8/2002 | Cooper | |
| 6,484,735 B1 | 11/2002 | Gordon | |
| 6,528,070 B1 * | 3/2003 | Bratescu | .................. A61K 8/06 424/401 |
| 7,192,601 B2 * | 3/2007 | Walker | ................... A61K 8/347 424/401 |
| 7,462,590 B2 | 12/2008 | Tichy | |
| 7,576,047 B2 | 8/2009 | Kilkenny | |
| 7,884,037 B2 * | 2/2011 | Sirovatka | ............. A61K 8/0208 442/102 |

(Continued)

FOREIGN PATENT DOCUMENTS

| | | |
|---|---|---|
| CA | 2111932 | 6/1994 |
| CA | 2246913 | 3/1999 |

(Continued)

OTHER PUBLICATIONS

Bacti-Stat AE—triclosan solution, Ecolab, 2010, 4 pages.
Betadine Surgical Scrub, 1 page.
Block, Disinfection, Sterilization and Preservation, 225-255, (1991).
ENDURE® 200 Healthcare Personnel Hand Wash, Ecolab, 2004, 1 page.
ENDURE® 400 Scrub-Stat 4 Foam Forming Solution, Surgical Hand Scrub and Healthcare Personnel Hand Wash, Ecolab, 2007, 4 pages.
ENDURE® 420 Cida-Stat Surgical Scrub/Healthcare Personnel Hand Wash, Ecolab, 2009, 5 pages.

(Continued)

*Primary Examiner* — Charles I Boyer
(74) *Attorney, Agent, or Firm* — 3M Innovative Properties Company

(57) ABSTRACT

Disclosed herein are methods for removing spores from skin, the method including dispensing an effective amount of a composition into or onto an article, wherein the composition includes water and from about 0.04 wt % to about 4 wt % polymeric cationic antimicrobial, nonionic antimicrobial or combinations thereof; contacting a skin surface with the composition; mechanically acting on the skin surface for at least one (1) second while the skin surface is in the presence of the composition; and removing at least a portion of the composition from the surface of the skin, wherein removing the composition also removes spores from the skin surface.

15 Claims, No Drawings

(56) References Cited

U.S. PATENT DOCUMENTS

| | | | |
|---|---|---|---|
| 2002/0076255 A1 | 6/2002 | Hoang | |
| 2002/0136768 A1* | 9/2002 | Staats | A61K 47/02 424/484 |
| 2003/0190371 A1* | 10/2003 | Graaf | A61K 8/0208 424/642 |
| 2005/0261159 A1 | 11/2005 | Parris | |
| 2006/0141017 A1 | 6/2006 | Kling | |
| 2006/0198876 A1 | 9/2006 | Tichy | |
| 2006/0204467 A1 | 9/2006 | Littau | |
| 2006/0205619 A1* | 9/2006 | Mayhall | A61K 8/416 510/130 |
| 2007/0020342 A1* | 1/2007 | Modak | A61K 8/27 424/642 |
| 2007/0054827 A1 | 3/2007 | Cheung | |
| 2007/0129641 A1 | 6/2007 | Sweeney | |
| 2007/0184016 A1* | 8/2007 | Macinga | A01N 33/12 424/78.27 |
| 2007/0244027 A1 | 10/2007 | Sivik | |
| 2008/0044479 A1 | 2/2008 | Stack | |
| 2008/0051314 A1* | 2/2008 | Wenzel | A61Q 3/02 510/507 |
| 2008/0095861 A1* | 4/2008 | Walker | A61K 8/347 424/616 |
| 2008/0102053 A1 | 5/2008 | Childers | |
| 2009/0004120 A1* | 1/2009 | Natsch | A61K 8/33 424/45 |
| 2009/0042870 A1* | 2/2009 | Fellows | A01N 39/00 514/224.8 |
| 2009/0069436 A1* | 3/2009 | MacGregor | A61K 8/416 514/635 |
| 2009/0170744 A1 | 7/2009 | Meine | |
| 2009/0181060 A1* | 7/2009 | Rosato | A61K 8/0208 424/402 |
| 2009/0291944 A1 | 11/2009 | Ash | |
| 2009/0301519 A1 | 12/2009 | Aubay | |
| 2009/0324737 A1* | 12/2009 | Walker | A61K 8/347 424/616 |
| 2010/0136069 A1 | 6/2010 | Deckner | |
| 2010/0216889 A1* | 8/2010 | Modak | A01N 31/02 514/635 |
| 2011/0117048 A1* | 5/2011 | Kritzler | A61K 31/327 424/78.07 |
| 2011/0123645 A1* | 5/2011 | Burt | A61K 31/205 424/719 |
| 2011/0152925 A1 | 6/2011 | Schorr | |
| 2011/0158922 A1* | 6/2011 | Dupont | A61P 17/10 424/59 |
| 2011/0182958 A1* | 7/2011 | Omidbakhsh | A01N 37/36 424/405 |
| 2011/0182959 A1 | 7/2011 | Cahill | |
| 2012/0201902 A1* | 8/2012 | Modak | A01N 31/02 424/618 |
| 2012/0276182 A1 | 11/2012 | Baker, Jr. | |
| 2013/0316993 A1* | 11/2013 | Santus | A61K 8/922 514/171 |
| 2014/0134124 A1* | 5/2014 | Huff | A61K 8/97 424/65 |
| 2014/0178444 A1* | 6/2014 | Stadler | C07H 15/04 424/401 |
| 2014/0336152 A1* | 11/2014 | Deckner | A47K 10/16 514/63 |
| 2014/0349902 A1* | 11/2014 | Allef | A61K 8/602 510/491 |
| 2015/0050342 A1* | 2/2015 | Lowe | A61K 31/555 424/489 |
| 2015/0086659 A1* | 3/2015 | Klofta | A47L 13/17 424/764 |
| 2015/0223464 A1 | 8/2015 | Bingham | |
| 2015/0305343 A1 | 10/2015 | Burke | |
| 2016/0058789 A1* | 3/2016 | Lentini | A01N 59/12 424/78.07 |
| 2016/0184354 A1* | 6/2016 | Ramirez | A61K 8/4913 424/59 |
| 2016/0354507 A1* | 12/2016 | Aviles | A61L 15/40 |
| 2017/0100318 A1* | 4/2017 | Wang | A61K 8/498 |
| 2017/0105417 A1* | 4/2017 | Roszell | A01N 25/02 |
| 2018/0168148 A1* | 6/2018 | Fellows | A01N 33/12 |
| 2018/0228904 A1* | 8/2018 | Kilic | A61K 47/34 |
| 2018/0353417 A1* | 12/2018 | Adkins, Jr. | A61K 9/0048 |
| 2019/0060201 A1* | 2/2019 | Cozean | A61K 31/155 |

FOREIGN PATENT DOCUMENTS

| | | |
|---|---|---|
| CA | 2621986 | 8/2008 |
| DE | 102004058143 | 5/2006 |
| EP | 0971997 | 1/2000 |
| EP | 2462806 | 6/2012 |
| KR | 20030085436 | 11/2003 |
| WO | WO 2000-30599 | 6/2000 |
| WO | WO 2002-102244 | 12/2002 |
| WO | WO 2003-002704 | 1/2003 |
| WO | WO 2003-066001 | 8/2003 |
| WO | WO 2006-013315 | 2/2006 |
| WO | WO 2006-084251 | 8/2006 |
| WO | WO 2008-003632 | 1/2008 |
| WO | WO 2009-050447 | 4/2009 |
| WO | WO 2009-112843 | 9/2009 |
| WO | WO 2010/097639 | 9/2010 |
| WO | WO 2014-008264 | 1/2014 |
| WO | WO 2017-003923 | 1/2017 |
| WO | WO 2017-112565 | 6/2017 |

OTHER PUBLICATIONS

Hibiclens Package Insert, Hibiclens® Antiseptic/Antimicrobial Skin Cleanser, Mölnlycke Health Care, 2006, 3 pages.
Medi-Scrub, Ecolab, 2010, 1 page.
SAGE® 2% Chlorhexidine Gluconate Cloth, Patient Preoperative Skin Preparation, 1 page.
International Search Report for PCT International Application No. PCT/US2016/67441, dated Mar. 3, 2017, 2 pages.
Necas et al., "Carrageenan: a review," 2013, *Cterianarni Medicina*, 58(4):187-205.
Nerzndzic et al., "Induced Sporicidal Activity of Chlorhexidine against Clostridium difficile Spores under Altered Physical and Chemical Conditions," Apr. 2015, *PLOS One*, 10(4):1-11 (e0123809).

\* cited by examiner

METHODS FOR SPORE REMOVAL COMPRISING A POLYSORBATE SURFACTANT AND CATIONIC ANTIMICROBIAL MIXTURE

CROSS REFERENCE TO RELATED APPLICATIONS

This application is a national stage filing under 35 U.S.C. 371 of PCT/US2016/067441, filed Dec. 19, 2016, which claims the benefit of U.S. Provisional Application No. 62/270,701, filed Dec. 22, 2015. The disclosures of both applications are incorporated by reference in their entirety herein.

FIELD

The present disclosure relates to methods of removing spores from skin.

BACKGROUND

There is a great deal of interest and urgency in preventing the spread of *C. difficile*, particularly in medical settings such as hospitals. Patients in a hospital setting often times develop *C. difficile* infections during or shortly after a course of antibiotics. While it is relatively easy to kill the vegetative form of *C. difficile*, the spore form of *C. difficile*, can be very difficult to kill. New technologies are therefore needed to address the problem of preventing the spread of *C. difficile*, between patients, health care workers, and the environment.

SUMMARY

Disclosed herein are methods for removing spores from skin, the method including dispensing an effective amount of a composition into or onto an article, wherein the composition includes water and from 0.04 wt % to 4 wt % polymeric cationic antimicrobial, nonionic antimicrobial or combinations thereof; contacting a skin surface with the composition; mechanically acting on the skin surface for at least one (1) second while the skin surface is in the presence of the composition; and removing at least a portion of the composition from the surface of the skin, wherein removing the composition also removes spores from the skin surface.

Also disclosed are methods for removing spores from skin, the method including dispensing an effective amount of a composition into a container, wherein the composition includes water and from 0.04 wt % to 4 wt % polymeric cationic antimicrobial, nonionic antimicrobial or combinations thereof; contacting a skin surface with the composition in the container; mechanically acting on the skin surface for at least one (1) second while the skin surface is in the presence of the composition; and removing at least a portion of the composition from the surface of the skin.

Also disclosed are methods for removing spores from skin, the method including obtaining a spore removing article, the spore removing article being capable of carrying an effective amount of a composition, wherein the composition includes water and from 0.04 wt % to 4 wt % polymeric cationic antimicrobial, nonionic antimicrobial or combinations thereof; contacting a skin surface with the spore removing article and the composition; mechanically acting on the skin surface for at least one (1) second with the spore removing article; and removing the spore removing article from the surface of the skin.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

In the following description of illustrative embodiments, reference is made to the accompanying figures which form a part hereof, and in which are shown, by way of illustration, specific embodiments. It is to be understood that other embodiments may be utilized and structural changes may be made without departing from the scope of the present disclosure.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, "top" and "bottom" (or other terms like "upper" and "lower") are utilized strictly for relative descriptions and do not imply any overall orientation of the article in which the described element is located.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another infusion device (such as a "first" substrate). Use of "first," "second," etc. in the description above and the claims that follow is also not necessarily intended to indicate that one comes earlier in time than the other.

Patients with *Clostridium difficile* infection (CDI) shed spores through fecal contamination, resulting in contamination of their skin, clothing, bedding, and environmental surfaces. It has been shown that contamination of multiple skin sites, including the chest, abdomen, arm, and hand, was common among patients with CDI and could easily be transferred to gloved hands. In addition, skin contamination often persisted after resolution of diarrhea. These data suggest that the skin of CDI patients may be an important source of transmission.

It has been shown that bathing with chlorhexidine gluconate is an effective way of reducing microbial burden on skin with pathogens such as vancomycin-resistant *Enterococcus* (VRE) and methicillin-resistant *Staphylococcus aureus*. However, it is known that bathing a patient with chlorhexidine gluconate wipe or a soap would not be useful for removal of spores.

Bathing becomes even more important when patients with CDI are not very mobile. In these cases, it is important to be able to remove or kill spores while the patient is in bed. Soaps that are commonly used in the market include soaps that are antimicrobial and non-antimicrobial. A non-antimicrobial soap like IVORY, for example, can be reasonably effective in removing spores; however, bacteria cannot be killed as with a non-antimicrobial soap. Chlorhexidine wipes (containing 2% chlorhexidine gluconate (CHG)) sold by Sage Corporation (Cary, Ill.) are being used in hospitals for daily patient bathing since they offer an effective way of killing vegetative bacteria. In some cases, a health care worker can use dilute bleach baths or wipes that have dilute bleach to clean the patient as hypochlorous acid has been shown to kill spores effectively. These solutions of dilute bleach need to be in wet contact with the skin of the patient for a few minutes to get an effective kill. Such exposure can be a concern however, because toxicity can build upon repeated use. Commonly owned U.S. Provisional Patent Application Ser. No. 62/187,372, filed Jul. 1, 2015 discloses the use of skin-friendly alcohol containing solutions.

It is therefore important to develop compositions and methods that are safe for repeated use on the skin; reduce spores to a level equivalent to that of the CDC recommended protocol (soap, water and paper towel); can be used on patients at their bed side; and may optionally have the ability to kill vegetative bacteria.

Disclosed herein are methods for removing spores that include steps of dispensing a composition, mechanically acting on a skin surface, and removing at least a portion of the composition from the surface of the skin. Compositions disclosed herein, e.g., compositions that can be utilized in disclosed methods can include water and an antimicrobial component. In some embodiments, useful compositions can also include an optional anionic thickener. For example, some illustrative compositions can include water, anionic thickener, and a cationic antimicrobial, a nonionic antimicrobial, or some combination thereof.

Water utilized in disclosed compositions can be deionized water, sterilized water, or both deionized and sterilized water for example. Compositions for use in disclosed methods can include various amounts of water. In some embodiments, compositions for use in disclosed methods can include not less than 40 wt % water. In some embodiments, compositions for use in disclosed methods can include not less than 70 wt % water. In some embodiments, composition for use in disclosed methods can include not less than 90 wt % water. In some embodiments, compositions for use in disclosed methods can include not greater than 99.96% water. In some embodiments, compositions for use in disclosed methods can include not greater than 99.5% water. In some embodiments, compositions for use in disclosed methods can include not greater than 99% water.

Disclosed compositions also include an antimicrobial component(s). The antimicrobial component can include polymeric cationic antimicrobials, nonionic antimicrobials or combinations thereof.

In some embodiments, disclosed compositions for use in disclosed methods can include polymeric cationic antimicrobials. "Polymer cationic antimicrobial" or "a polymeric cationic antimicrobial" may also refer to more than one type of polymeric cationic antimicrobial. Polymeric cationic antimicrobials that can be utilized in disclosed compositions and methods can include cationic quaternary ammonium salts for example.

Cationic quaternary ammonium salts can include, for example, polymers having quaternary amine groups with at least one alkyl or aralkyl chain of at least 6 carbon atoms and in some embodiments at least 8 carbon atoms. The polymers may be linear, branched, hyperbranched or dendrimers. Some illustrative antimicrobial polymeric quaternary amine polymers include those described in U.S. Pat. Nos. 6,440,405; 5,408,022; and 5,084,096; PCT Publication No. WO2002/102244; and Disinfection, Sterilization and Preservation, S. Block, 4th ed., 1991, Chapter 13, Lea & Febiger, the disclosures of which are incorporated herein by reference.

In some embodiments, one useful class of polymeric quaternary ammonium antiseptic compounds include polybiguanides. Compounds of this class can be represented by the formula:

X—$R^1$—NH—C(NH)—NH—C(NH)—NH—$R^2$—NHC(NH)—NH—C(NH)—NH—$R^3$—X where $R^1$, $R^2$, and $R^3$ are bridging groups such as polymethylene groups preferably having 2 to 10 methylene groups, more preferably 4 to 8 methylene groups and most preferably 6 methylene groups. The methylene groups can be optionally substituted in available positions with halogen, hydroxyl, or phenyl groups. X is a terminal group and is typically an amine, amine salt, or a dicyandiamide group. A specific illustrative compound of this class is polyhexamethylene biguanide (PHMB) commercially available as Cosmocil CQ from Aveci, Wilmington, Del.

In some embodiments, compositions can include not less than 0.02 wt % polymeric cationic antimicrobial. In some embodiments, compositions can include not less than 0.04 wt % polymeric cationic antimicrobial. In some embodiments compositions composition can include not greater than 0.3 wt % polymeric cationic antimicrobial. In some embodiments compositions composition can include not greater than 1 wt % polymeric cationic antimicrobial In some embodiments, disclosed compositions for use in disclosed methods can include nonionic antimicrobials. Nonionic antimicrobials ("nonionic antimicrobial" or "a nonionic antimicrobial" may also refer to more than one type of nonionic antimicrobial) that can optionally be utilized in disclosed compositions and methods can include 5-chloro-2(2,4-dichlorophenoxy)phenol (also referred to as triclosan), chrloroxyenol (4-chloro-3,5-dimethylphenol) (also referred to as PCMX), benzyl alcohol, phenoxyethanol, and the like. In some embodiments, compositions can include not greater than 4 wt % nonionic antimicrobial. In some embodiments, compositions can include not greater than 1.5 wt % nonionic antimicrobial. In some embodiments, compositions can include not less than 0.5 wt %. In some embodiments, compositions can include not less than 1 wt %.

In some embodiments, disclosed compositions for use in disclosed methods do not include cationic antimicrobials that are not polymeric. Illustrative non-polymeric cationic antimicrobials can include, for example cetyl pyridinium chloride, cetrimonium bromide (CTAB), behentrimonium chloride, benzothonium chloride, bis-biguanides include chlorhexidine salts such as benzethonium chloride, chlorhexidine salts such as chlorhexidine gluconate (CHG), octenidine salts such as octenidine dihydrochloride, and stearalkonium chloride. Therefore, in some embodiments, compositions for use in disclosed methods are free of non-polymeric cationic antimicrobials.

Non-polymeric cationic antimicrobials are generally utilized to kill bacteria, but are generally not known to kill spores. CDC and WHO guidelines recommend hand washing with soap, water and paper towel for CDI rooms. The type of soap is not specified by the guidelines, but hospitals are increasingly using antimicrobial soaps instead of regular soaps in wards, ICUs, peri-operative spaces, physicians' lounges, etc. Some antimicrobial soaps can have high concentrations of non-polymeric cationic antimicrobials or non-ionic antimicrobials. The inventors of the instant compositions and methods unexpectedly found that the addition of non-polymeric cationic antimicrobials, in such concentrations can detrimentally affect spore removal.

In some embodiments, compositions that can be utilized in disclosed methods can be compositions that are free of non-polymeric cationic antimicrobials. Non-polymeric cationic antimicrobials can be defined as an antimicrobial. In some embodiments, a non-polymeric cationic antimicrobial can include compound that has a charge of not greater than +2/molecule and has a molecular weight under 1000. In some embodiments, illustrative non-polymeric cationic antimicrobials can include CHG and BKC. In some embodiments, such compositions (those that are free of non-polymeric cationic antimicrobials) may or may not include polymeric cationic antimicrobials.

In some embodiments, compositions that can be utilized in disclosed methods are free of an inorganic non-ionic antimicrobial that is not charged and is not associated with an anionic species. In some embodiments, a composition can be free of iodine or an iodine containing species.

Mixtures of polymeric cationic antimicrobials and non-ionic antimicrobials can also be utilized in compositions. In some embodiments, disclosed compositions for use in disclosed methods can be characterized by the total amount, if any of antimicrobial (polymeric cationic, nonionic, or the combination thereof) present. In some embodiments, a composition for use in disclosed methods can include, if present, not greater than 4 wt % total antimicrobial. In some embodiments, a composition for use in disclosed methods can include, if present, not less than 0.04 wt % total antimicrobial.

Disclosed compositions can also include other optional components, illustrative optional components can include, for example anionic thickeners, alcohols, surfactants, humectants, emulsifiers, skin conditioning agents and abrasives or polishing agents.

One optional component includes anionic thickeners. "An anionic thickener" or "anionic thickener" may also refer to more than one type of anionic thickener. Anionic thickeners that can optionally be utilized in disclosed compositions and methods can include, but are not limited to, natural polysaccharides, synthetic carbomers, or combinations thereof. Particular natural anionic thickeners that can be used can include gums or pectin for example. Specific anionic thickeners that can be used can include xanthan gum, carrageenan, alginic acid, pectin and carboxymethyl cellulose sodium salt, glycosaminoglycans such as chondroitin sulfate, heparin, similar compounds, and combinations thereof. Mixtures of more than one anionic thickener can also be utilized in compositions, as such use of "an anionic thickener" can imply one or more than one specific anionic thickener.

Arabinoxylans, beta-glucans, chitin, galacatomannans like guar gum, locus bean gum etc., glucomannans, agar, cellulose and the like that are neutral may be detrimental to spore removal.

The "polyanion characteristics" differed from gum to gum, e.g., the number of anionic groups on the polymer (acid equivalent weight) and the proportion in the salt and acid forms. The polyanionic characteristics of the compound may influence the viscosity of the solution which could have an indirect effect on spore removal. The viscosity of the gum increases as it is changed from the acid to the salt form, e.g., as the pH is increased. In the salt form, the polysaccharide can assume a more extended configuration. The anionic groups could include a carboxylate, sulfate, sulfonate or a phosphate. Specific anionic gums could include xanthan gum, alginic acid, sodium alginate, ammonium alginate, propyleneglycol alginate, iota-, kappa-, or lambda-carrageenan, gum ghatti, karaya gum, tragacanth gum, gum arabic, pectin, alkoxycelluloses, carboxymethyl guar or carboxymethyl locust bean gum. Anionic polyelectrolytes that are anionic polymers could also be utilized, with a linear or branched structure, with anionic groups distributed along the polymeric chain, optionally present also in the chain end groups.

In compositions where a natural polysaccharide is utilized, it can be described by its equivalent weight, defined as molecular weight/number of anionic groups present in the polysaccharide. In some embodiments, useful polysaccharides can have an equivalent weight of not less 150, in some embodiments not less than 200, or in some embodiments not less than 250.

The anionic charges of the anionic thickener may result from the incorporation of an anionic monomer into the polymer, for example. Non-limiting examples of suitable anionic monomers can include: acrylic acid, methacrylic acid, 3-(sulfopropyl)-acrylate potassium salt, 3-(sulfopropyl)-methacrylate potassium salt, 2-acrylamido-2-methylpropanesulfonic acid, crotonic acid, sodium vinyl sulfonate, acrylamidoglycolic acid, 2-acrylamido-2-methylbutanoic acid, 2-acrylamido-2-methylpropanephosphonic acid, sodium vinyl phosphonate, allyl phosphonic acid and salts thereof. Illustrative examples can include polymers of CARBOPOL, AMPHOMER® polymeric resin, BALANCE® CR (acrylates copolymer), FLEXAN® 130 (sodium polystyrene sulfonate) polymers, and RESYN® 28-2930 (vinyl acrylate/crotonates/vinyl deodeconate copolymer) resin. The equivalent weight of useful anionic polyelectrolytes may be not greater than 10,000, in some embodiments not greater than 3,000, and in some embodiments not greater than 1,500.

Compositions that include thickeners other than anionic, for example cationic or non-ionic may not aid in spore removal and may in fact be detrimental to spore removal. Given that spores have a mild negative charge, it is surprising that a thickener with a negative charge would be more effective in spore removal than would a thickener with a positive charge or no charge. One would not expect the addition of an anionic thickener with or without low levels of cationic or nonionic antimicrobials to assist in spore removal.

Disclosed compositions and compositions for use in disclosed methods, if an optional thickener is included, can include an anionic thickener at various levels. In some embodiments, compositions include not greater than 5 wt % anionic thickener. In some embodiments, compositions include not greater than 4 wt % anionic thickener. In some embodiments, compositions include not greater than 2 wt % anionic thickener. In some embodiments, compositions include not less than 0.05 wt % anionic thickener. In some embodiments, compositions include not less than 0.1 wt % anionic thickener. In some embodiments, compositions include not less than 0.5 wt % anionic thickener. Thickeners that have lower viscosities may be able to be used at higher levels than those with higher viscosities, for example.

Disclosed compositions and compositions for use in disclosed methods can optionally include an alcohol ("an alcohol" or "alcohol" may also refer to more than one type of alcohol). Any kind of alcohol can optionally be utilized in disclosed compositions and methods. In some embodiments, a lower hydrocarbon chain alcohol such as a $C_2$-$C_5$ alcohol can be utilized. In some embodiments the alcohol can be chosen from ethanol and isopropanol, and in some embodiments ethanol. Ethanol may be useful because it may provide a broad spectrum and quick kill of microbes and an odor acceptable to consumers such as doctors, nurses and clinicians. Propyl alcohol (1-propanol) may also be used. A blend of two or more lower alcohols may also be utilized. The lower alcohols may be denatured, such as for example, denatured ethanol including SDA-3C (commercially available from Eastman Chemical, Kingsport, Tenn.). Co-solvents may be further included in the composition with the lower alcohol. Considering likely applications contemplated, suitable co-solvents can include for example acetone, hydrocarbons such as isooctane, glycols, ketones, ethers, and short chain esters.

In disclosed compositions and compositions for use in disclosed methods, alcohol, if included can be included in various amounts. In some embodiments, if disclosed compositions include an alcohol, the composition can include not greater than 50 wt % of an alcohol, not greater than 40 wt % of an alcohol, or not greater than 20 wt % of an alcohol. In some embodiments, if disclosed compositions include an alcohol, the composition can include not less than 2 wt % of an alcohol, or not less than 5 wt % of an alcohol.

Disclosed compositions and compositions for use in disclosed methods can optionally include a surfactant ("a surfactant" or "surfactant" may also refer to more than one type of surfactant). Any kind of surfactant can optionally be utilized in disclosed compositions and methods. In some embodiments, disclosed compositions can be in the form of a soap. In some embodiments, soap like compositions can include a surfactant as a base, in some embodiments an aqueous one. Surfactant bases can function to dissolve the ampholyte(s) in the aqueous medium, for example. Suitable surfactants can include, but are not limited to, amphoteric surfactants, nonionic surfactants, zwitterionic surfactants, or any combination thereof.

Illustrative amphoteric or zwitterionic surfactants can include aliphatic secondary or tertiary amine derivatives, specifically those in which the aliphatic radical is a linear or branched chain containing 8 to 18 carbon atoms and containing at least one water-solubilizing anionic group (for example carboxylate, sulfonate, sulfate, phosphate or phosphonate); carboxybetaines; (C8-C20) alkylbetaines; sulfobetaines; (C8-C20); alkylamido (C1-C6) alkylbetaines; and (C8-C20) alkylamido (C1-C6) alkylsulfobetaines. Useful amphoteric or zwitterionic surfactants could also include amidobetaines and amidosulfobetaines for example. Useful zwitterionic surfactants can include the derivatives of aliphatic quaternary ammonium, phosphonium, and sulfonium compounds, specifically those in which the aliphatic radicals are straight or branched, and wherein one of the aliphatic substituents contains from about 8 to 18 carbon atoms and one contains an anionic group, e.g., carboxy, sulfonate, sulfate, phosphate or phosphonate.

Illustrative non-ionic surfactants can include condensates of sorbitan monostearate with ethylene oxide, condensates of ethylene oxide with propylene oxide, and condensates of propylene glycol (available under the tradename PLURONICS®). Other examples of water-soluble non-ionic surfactants useful herein can include condensation products of ethylene oxide with various other compounds which are reactive therewith and have long hydrophobic chains (e.g. C12-C20 aliphatic chains), such condensation products (ethoxamers) may contain hydrophilic polyoxyethylene moieties, such as condensation products of polyethylene oxide with fatty acids, fatty alcohols, fatty amides, or polyhydric alcohols (e.g. sorbitan monostearate). Specific examples include decyl glucosides, polysorbates, EO/PO block copolymers such as PLURONICS®.

In disclosed compositions and compositions for use in disclosed methods, surfactant, if included can be included in various amounts. In some embodiments, if disclosed compositions include a surfactant, the composition can include not greater than 15 wt % of a surfactant, not greater than 5 wt % of a surfactant, or not greater than 3 wt % of a surfactant. In some embodiments, if disclosed compositions include a surfactant, the composition can include not less than 0.5 wt % of a surfactant, or not less than 0.1 wt % of a surfactant.

Disclosed compositions and compositions for use in disclosed methods can optionally include a humectant ("a humectant" may also refer to more than one type of humectant). Any kind of humectant can optionally be utilized in disclosed compositions and methods. Suitable humectants may include for example glycerin, propylene glycol, sorbitol, polypropylene glycol, polyethylene glycol, and combinations thereof. Various amounts of humectants could be utilized in disclosed compositions.

Disclosed compositions and compositions for use in disclosed methods can optionally include a skin conditioning agent ("a skin conditioning agent" may also refer to more than one type of skin conditioning agent). Any kind of skin conditioning agent can optionally be utilized in disclosed compositions and methods. Suitable skin conditioning agents such as glycerides, sorbitol, castor oil, allantoin, lanolin and its derivatives, cetyl alcohol and cationic polymers could be utilized for example. Various amounts of skin conditioning agents could be utilized in disclosed compositions.

Disclosed compositions and compositions for use in disclosed methods can optionally include an abrasive or exfoliating material ("abrasive or polishing material" may also refer to more than one type of abrasive and/or polishing material). In some embodiments abrasive or polishing materials could include water insoluble abrasives such as phosphates, carbonates, silicates, hydrated silica, hydrated alumina, bentonite, as well as polymeric beads such a poly methyl methacrylate (PMMA), polystyrene, and polyolefin beads and particulates and the like as well as mixtures thereof. In some cases, other mild exfoliating agents could optionally be used in disclosed compositions for mechanically removing spores. Illustrative exfoliating agents could include arrowroot powder or walnut powder for example. Various amounts of abrasive or polishing material could be utilized in disclosed compositions.

In some embodiments, the pH of the composition can be controlled and/or modified. In some embodiments useful compositions or compositions useful in disclosed methods can have a pH of not less than 3, or in some embodiments not less than 5 for example. In some embodiments useful compositions or compositions useful in disclosed methods can have a pH of not greater than 10, or in some embodiment not greater than 9 for example.

In some embodiments, the temperature of the composition can be controlled and/or modified. In some embodiment useful compositions or compositions useful in disclosed methods can have a temperature that is not less than room temperature (about 25° C.), or in some embodiments higher than room temperature. In some embodiments, useful compositions or compositions useful in disclosed methods can have a temperature that is not so high that it is not tolerated by skin (for example not greater than 40° C., or more specifically not greater than 38° C.). In some embodiments methods that will be disclosed heretofore can include steps of heating a composition or heating an article which a composition (either heated or not) has been dispensed into or onto.

Disclosed methods include a step of dispensing a composition. The composition can be dispensed into or onto an article. Dispensing can be accomplished via pouring, spraying, bringing the article into the composition (e.g., dipping), or submerging the article in the composition, for example. As indicated, the composition can be dispensed into or onto an article.

In embodiments where the composition is dispensed into an article, illustrative articles can include for example basins, bowls, and tubs. Such methods can be useful in instances where the skin from which the spores are to be removed is to be brought into contact with the composition in the article, for example. More specifically, this can be useful if some part of, or all of the patient is going to be immersed in the composition in the article. For example, the patient could be going to bathe in the article (e.g., a tub). Another example could include a basin where some part of a patient, for example one or more hands are to be immersed in the composition in the basin. This can also be useful if a secondary article is going to be immersed in the composition in the article and then that secondary article is going to be brought into contact with the skin.

The amount of the composition dispensed into an article, or an effective amount, can depend at least in part on how the skin from which the spores are to be removed is to be brought into contact with the composition in the article, the particular skin to be cleaned, the type of mechanical action (discussed below), whether or not there is a secondary article, or combinations thereof.

In some embodiments where the composition is to be dispensed into an article, not less than 5 milliliters (mL) of composition can be dispensed into an article, not less than 10 mL of composition, not less than 20 mL of composition, or not less than 50 mL of composition. Relevant upper amounts of composition would depend at least in part on the particular article (e.g., its maximum volume), the volume to be immersed (if immersion is relevant) in the article, and combinations thereof.

In some embodiments where the composition is to be dispensed into an article, the amount dispensed, or an effective amount can also depend, at least in part, on the surface area of skin from which spores are to be removed. In some embodiments, not less than 1 mL/10 cm$^2$ of skin surface from which spores are to be removed can be dispensed into the article, and in some embodiments not less than 1 mL/50 cm$^2$ of skin surface from which spores are to be removed can be dispensed into the article.

The composition can also be dispensed onto an article. In embodiments where the composition is dispensed onto an article, illustrative articles can include for example wipes, sponges, cloths, loofahs, brushes, pads, or fibrous mats for example. It should be understood that dispensing a composition into an article can imply brining the composition to the article, bringing the article to the composition, or any combination thereof. Such methods can be useful in instances where the skin from which the spores are to be removed is to be brought into contact with an article that is associated with the composition, for example. More specifically, this can be useful for wiping affected skin of a patient with the article to which the composition has been dispensed, to remove spores from the skin of the patient.

The amount of the composition dispensed onto an article, or an effective amount, can depend at least in part on the particular skin to be cleaned, the total surface area of skin to be cleaned, the type of mechanical action (discussed below), the particular type of article (e.g., the amount the article can absorb, hold, etc.) or combinations thereof.

In some embodiments where the composition is to be dispensed onto an article, not less than 30 mL of composition can be dispensed onto an article, not less than 40 mL of composition, not less than 50 mL of composition, or not less than 20 mL of composition. Relevant upper amounts of composition would depend at least in part on the particular article (e.g., its surface area, the material thereof, its porosity, etc.), a desired level of "wetness" of the article, and combinations thereof.

In some embodiments where the composition is to be dispensed onto an article, the amount dispensed, or an effective amount can also depend, at least in part, on the surface area of skin from which spores are to be removed. In some embodiments, not less than 1 mL/10 $cm^2$ of skin surface from which spores are to be removed can be dispensed onto the article, and in some embodiments not less than 5 mL/10 $cm^2$ of skin surface from which spores are to be removed can be dispensed onto the article.

In some embodiments where the composition is to be dispensed onto an article, an effective amount is one which provides a sufficient amount of composition in contact with the skin surface from which spores are to be removed. In some embodiments, an effective amount can be described with respect to the amount of the composition necessary to saturate the article. An article is "saturated" when the article is contacted with more composition than the article can hold and reasonable pressure is applied to the article to remove the excess. In articles that are easily wet, "saturation" can be determined substantially immediately after incorporation. In articles that are more hydrophobic, it may be necessary to expose the article to the composition for a longer period of time. A reasonable amount of pressure can be that applied with an average hand squeezing motion until no further solution is seen dripping from the wipe. The amount of composition retained in the article after pressure has been applied can be referred to as the saturation amount.

In some embodiments, an effective amount of composition that can be dispensed onto an article can be an amount that renders the wipe as wet as possible so that the saturation amount is bypassed. In some embodiments, it may not be desirable to go below the saturation level, or not less than 5% below the saturation amount. In some embodiments, an effective amount of composition that can be dispensed onto an article can be not greater than 40% above the saturation amount of the article. In some embodiments, an effective amount can be not greater than 20% above the saturation amount of the article, in some embodiments not greater than 15% above the saturation amount, and in some embodiments not greater than 5% above the saturation amount. In some embodiments, an effective amount of a composition can be one that makes the article as wet as possible while maintaining a useful article.

For the purposes of illustration only, a 4 inch×6 inch SONTARA® 8005, 100% PET (DuPont) wipe has a saturation amount of 3.5 g liquid, so illustrative effective amounts for such an article could include not greater than 4.9 g of liquid, not greater than 4.2 g liquid, not greater than 4.0 g liquid, not greater than 3.7 g liquid, and not less than 3.3 g liquid.

In some embodiments, a different first step (as opposed to the first step discussed above, dispensing a composition into or onto an article) can be utilized. For example, in some embodiments, a first step can include obtaining a spore removing article. A spore removing article is an article that is capable of carrying an effective amount of a composition distributed throughout the material of the article.

The step of obtaining a spore removing article can be accomplished by contacting a carrier with a composition, such as those compositions described above. This step can be carried out as discussed above with respect to dispensing the composition onto an article, which in this case is the carrier. The carrier can be a wipe, or a sponge for example. Also as discussed above, the carrier can be dipped into the composition, the composition can be sprayed onto the carrier, the composition can be applied to the composition, or any combination thereof.

The step of obtaining a spore removing article can also alternatively be accomplished by obtaining a carrier pre-moistened with the composition. For example, one or more spore removing articles can be packaged together in any type of air tight or re-sealable packaging, for example a foil pack, a plastic container, or any combination thereof.

Disclosed methods also include steps of contacting the skin from which the spores are to be removed with the composition. Details regarding this step can vary based at least in part on whether the composition was dispensed into an article or onto an article, the type of article, the skin to be contacted, or combinations thereof. In some embodiments where the composition is dispensed into an article, this step can be accomplished by immersing the skin from which the spores are to be removed in the composition in the article (e.g., immersing the skin in a tub or basin). In some embodiments where the composition is dispensed onto an article, this step can be accomplished by contacting the article with the skin or vice versa (e.g., contacting a composition containing wipe with the skin). The skin surface can be any portion of a patient's skin that has spores thereon, is thought to have spores thereon, may have spores thereon, or any combination thereof.

Disclosed methods also include a step of mechanically acting on the skin surface or subjecting the skin to mechanical action. The mechanical action can occur while the skin surface is in the presence of the composition, or while the skin is in contact with some portion of the composition. Virtually any type of mechanical action could be utilized in disclosed methods. Illustrative types of mechanical action can include, for example, rubbing the skin (for example rubbing the skin with the article onto which the composition was dispensed, rubbing the skin with an article not treated with the composition, rubbing the skin with some other portion of the skin, or any combination thereof), wiping the skin (e.g., moving the article onto which the composition was dispensed, moving an article not treated with the composition, moving additional skin over the skin from which the spores are to be removed, or any combination thereof). In some embodiments, mechanical action can include rubbing, wiping, scouring, sliding, scraping, or exfoliating (for example) the surface with the article onto which the composition was dispensed or a different article. In some embodiments, mechanical action can include moving a first surface contacted with the composition across or over a second surface contacted with the composition. A specific example of such an embodiment can include rubbing two hands contacted with the composition together.

The step of subjecting the surface to mechanical action can occur for any amount of time. In some embodiments, the surface can be subjected to mechanical action for not less than 1 second, not less than 5 seconds, not less than 10 seconds, or not less than 20 seconds. In some embodiments, the surface can be subjected to mechanical action for not greater than 2 minutes, or not greater than 1 minute, for example.

The steps of contacting the skin with a composition and subjecting the skin in contact with the composition to mechanical action can occur with at least some overlap. For example, in some embodiments, while at least some of the composition is being contacted with the skin, mechanical action can begin. Specifically, for example, while a hand, or hands, is being dipped into the composition (or even soaked in the composition), the hands can be rubbed together. Either (or both) of the steps of contacting the skin with the composition or subjecting the skin to mechanical action can be repeated more than once in some embodiments.

In some embodiments, the step of subjecting the skin to mechanical action can be described by the force of the mechanical action. In some embodiments, the mechanical action on the skin have a force of not less than 20 N.

Disclosed methods also include a step of removing at least a portion of the composition from the skin. Removing this portion of the composition also removes at least some spores from the skin. In some embodiments, this step is accomplished without an excess of water, for example without rinsing under running water or without rinsing in additional water (e.g., water in a basin).

The step of removing a portion of the composition from the skin can leave some portion of the composition on the skin surface. In some embodiments, not greater than 3 mL of composition remains on the skin surface, or in some embodiments not greater than 1 mL of composition remains on the skin surface. In some embodiments, the composition does not substantially evaporate from the skin surface, but has to be removed via some other action.

Disclosed compositions and methods can be utilized on skin of patients, health care workers, other individuals, or any combination thereof. Disclosed methods can be utilized with various compositions, including those disclosed herein.

Illustrative disclosed embodiments are provided below.

Some illustrative embodiments can include methods for removing spores from skin, the methods comprising: dispensing an effective amount of a composition into or onto an article, wherein the composition comprises: water; and from about 0.04 wt % to about 4 wt % polymeric cationic antimicrobial, nonionic antimicrobial or combinations thereof; contacting a skin surface with the composition; mechanically acting on the skin surface for at least one (1) second while the skin surface is in the presence of the composition; and removing at least a portion of the composition from the surface of the skin, wherein removing the composition also removes spores from the skin surface.

Such methods, wherein the composition comprises from about 0.04 wt % to about 0.3 wt % polymeric cationic antimicrobial. Such methods, wherein the cationic antimicrobial is PHMB, or some combination thereof. Such methods, wherein the composition comprises from about 0.5 wt % to about 4 wt % nonionic antimicrobial. Such methods, wherein the nonionic antimicrobial is triclosan, PCMX, benzyl alcohol, phenoxyethanol, or some combination thereof. Such methods, wherein the composition is dispensed into an article. Such methods, wherein the article is a basin, bowl, or tub. Such methods, wherein at least about 5 mL of composition is dispensed into the article. Such methods, wherein at least about 10 mL of composition is dispensed into the article. Such methods, wherein at least about 20 mL of composition is dispensed into the article. Such methods, wherein at least about 50 mL of composition is dispensed into the article. Such methods, wherein at least about 1 mL/10 $cm^2$ of the skin surface to be cleaned is dispensed into the article. Such methods, wherein at least about 1 mL/50 $cm^2$ of the skin surface to be cleaned is dispensed into the article. Such methods, wherein the composition is dispensed onto an article. Such methods, wherein the article is a wipe, a sponge, or a fibrous mat. Such methods, wherein at least about 1 mL/$cm^2$ to 10 mL/$cm^2$ of the skin surface to be cleaned is dispensed onto the article. Such methods, wherein at least about 3 mL/$cm^2$ to 10 mL/$cm^2$ of the skin surface to be cleaned is dispensed onto the article. Such methods, wherein the effective amount of composition is not more than about 40% of a saturation amount of the article. Such methods, wherein the effective amount of composition is not more than about 20% of a saturation amount of the article. Such methods, wherein the effective amount of composition is not more than about 15% of a saturation amount of the article. Such methods, wherein the effective amount of composition is not less than about 20% of a saturation amount of the article. Such methods, wherein the effective amount of composition is not less than about 15% of a saturation amount of the article. Such methods, wherein the mechanical action lasts for at least about 5 seconds. Such methods, wherein the mechanical action lasts for at least about 15 seconds. Such methods, wherein the mechanical action lasts for at least about 30 seconds. Such methods, wherein mechanically acting on the skin has a force of at least about 20 N. Such methods, wherein mechanically acting comprises rubbing, wiping, scrubbing, pulsing, sliding or some combination thereof. Such methods, wherein the step of removing is accomplished without an excess of water. Such methods, wherein the step of removing leaves less than 3 mL of composition on the surface. Such methods, wherein the step of removing leaves less than 1 mL of composition on the surface. Such methods, wherein the composition further comprises from about 0.1 wt % to about 4 wt % anionic thickener. Such methods, wherein the anionic thickener is selected from natural polysaccharides, synthetic carbomers, or combinations thereof. Such methods, wherein the anionic thickener is a gum, a pectin, or a combination thereof. Such methods, wherein the anionic thickener is xanthan, carrageenan, alginic acid, or some combination thereof. Such methods, wherein the composition further comprises a lower hydrocarbon chain alcohol. Such methods, wherein the lower chain alcohol is a $C_2$ to $C_5$ alcohol, or mixture thereof. Such methods, wherein the composition comprises from about 2 to about 20 wt % of the lower hydrocarbon chain alcohol. Such methods, wherein the composition comprises not greater than about 50 wt % of the lower hydrocarbon chain alcohol. Such methods, wherein the composition further comprises a surfactant. Such methods, wherein the composition comprises not greater than about 15 wt % surfactant.

Such methods, wherein the composition further comprises humectants, emulsifiers, or combinations thereof. Such methods, wherein the composition is free of a non-polymeric cationic antimicrobial.

Additional illustrative embodiments can include methods comprising: dispensing an effective amount of a composition into a container, wherein the composition comprises: water; and from about 0.04 wt % to about 4 wt % polymeric cationic antimicrobial, nonionic antimicrobial or combinations thereof; contacting a skin surface with the composition in the container; mechanically acting on the skin surface for at least one (1) second while the skin surface is in the presence of the composition; and removing at least a portion of the composition from the surface of the skin.

Such methods, wherein the composition comprises from about 0.04 wt % to about 0.3 wt % polymeric cationic antimicrobial. Such methods, wherein the cationic antimicrobial is PHMB. Such methods, wherein the composition comprises from about 0.5 wt % to about 4 wt % nonionic antimicrobial. Such methods, wherein the nonionic antimicrobial is triclosan, PCMX, benzyl alcohol, phenoxyethanol, or some combination thereof. Such methods, wherein the container is a basin, bowl, or tub. Such methods, wherein at least about 5 mL of composition is dispensed into the container. Such methods, wherein at least about 10 mL of composition is dispensed into the container. Such methods, wherein at least about 20 mL of composition is dispensed into the container. Such methods, wherein at least about 50 mL of composition is dispensed into the container. Such methods, wherein at least about 1 mL/10 $cm^2$ of the skin surface to be cleaned is dispensed into the container. Such methods, wherein at least about 1 mL/50 $cm^2$ of the skin surface to be cleaned is dispensed into the container. Such methods, wherein the mechanical action lasts for at least about 5 seconds. Such methods, wherein the mechanical action lasts for at least about 15 seconds. Such methods, wherein the mechanical action lasts for at least about 30 seconds. Such methods, wherein mechanically acting on the skin has a force of at least about 20 N. Such methods, wherein mechanically acting comprises rubbing, wiping, scrubbing, pulsing, sliding or some combination thereof. Such methods, wherein the step of removing is accomplished without an excess of water. Such methods, wherein the step of removing leaves less than 3 mL of composition on the surface. Such methods, wherein the step of removing leaves less than 1 mL of composition on the surface. Such methods, wherein the composition further comprises from about 0.1 wt % to about 4 wt % anionic thickener. Such methods, wherein the anionic thickener is selected from natural polysaccharides, synthetic carbomers, or combinations thereof. Such methods, wherein the anionic thickener is a gum, a pectin, or a combination thereof. Such methods, wherein the anionic thickener is xanthan, carrageenan, alginic acid, or some combination thereof. Such methods, wherein the composition further comprises a lower hydrocarbon chain alcohol. Such methods, wherein the lower chain alcohol is a $C_2$ to $C_5$ alcohol, or mixture thereof. Such methods, wherein the composition comprises from about 2 to about 20 wt % of the lower hydrocarbon chain alcohol. Such methods, wherein the composition comprises not greater than about 50 wt % of the lower hydrocarbon chain alcohol. Such methods, wherein the composition further comprises a surfactant. Such methods, wherein the composition comprises not greater than about 5 wt % surfactant. Such methods, wherein the composition further comprises humectants, emulsifiers, or combinations thereof. Such methods, wherein the composition is free of a non-polymeric cationic antimicrobial.

Additional illustrative embodiments can include methods comprising: obtaining a spore removing article, the spore removing article being capable of carrying an effective amount of a composition, wherein the composition comprises: water; and from about 0.04 wt % to about 4 wt % polymeric cationic antimicrobial, nonionic antimicrobial or combinations thereof contacting a skin surface with the spore removing article and the composition; mechanically acting on the skin surface for at least one (1) second with the spore removing article; and removing the spore removing article from the surface of the skin.

Such methods, wherein the composition comprises from about 0.04 wt % to about 0.3 wt % polymeric cationic antimicrobial. Such methods, wherein the cationic antimicrobial is PHMB. Such methods, wherein the composition comprises from about 0.5 wt % to about 4 wt % nonionic antimicrobial. Such methods, wherein the nonionic antimicrobial is triclosan, PCMX, benzyl alcohol, phenoxyethanol, or some combination thereof. Such methods, wherein the step of obtaining a spore removing article comprises contacting a carrier with the composition. Such methods, wherein the carrier is a wipe, a sponge, or a fibrous mat. Such methods, wherein the step of contacting the carrier with the composition comprises dipping the carrier in the composition, spraying the composition onto the carrier, or some combination thereof. Such methods, wherein the step of obtaining a spore removing article comprises obtaining a carrier pre-moistened with the composition. Such methods, wherein the step of obtaining a spore removing article comprises obtaining the spore removing article from a package comprising a plurality of spore removing articles. Such methods, wherein the package comprises a foil pack, a plastic container, or some combination thereof. Such methods, wherein the spore removing article is capable of carrying at least about 5 mL of composition. Such methods, wherein the spore removing article absorbs the composition, holds the composition, or some combination thereof. Such methods, wherein the amount of composition in contact with the skin surface during the contacting step is at least about 5 mL. Such methods, wherein the amount of composition in contact with the skin surface during the contacting step is at least about 10 mL. Such methods, wherein the amount of composition in contact with the skin surface during the contacting step is not greater than about 50 mL. Such methods, wherein the amount of composition in contact with the skin surface during the contacting step is at least about 1 mL/10 cm$^2$ of the skin surface to be cleaned. Such methods, wherein the composition further comprises from about 0.1 wt % to about 4 wt % anionic thickener. Such methods, wherein the anionic thickener is selected from natural polysaccharides, synthetic carbomers, or combinations thereof. Such methods, wherein the anionic thickener is a gum, a pectin, or a combination thereof. Such methods, wherein the anionic thickener is xanthan, carrageenan, alginic acid, or some combination thereof. Such methods, wherein the mechanical action lasts for at least about 5 seconds. Such methods, wherein the mechanical action lasts for at least about 15 seconds. Such methods, wherein the mechanical action lasts for at least about 30 seconds. Such methods, wherein mechanically acting on the skin has a force of at least about 20 N. Such methods, wherein mechanically acting comprises rubbing, wiping, scrubbing, pulsing, sliding or some combination thereof. Such methods, wherein the step of removing is accomplished without an excess of water. Such methods, wherein the step of removing leaves less than 3 mL of composition on the surface. Such methods, wherein the step of removing leaves less than 1 mL of composition on the surface. Such methods, wherein the composition further comprises a lower hydrocarbon chain alcohol. Such methods, wherein the lower chain alcohol is a $C_2$ to $C_5$ alcohol, or mixture thereof. Such methods, wherein the composition comprises from about 2 to about 20 wt % of the lower hydrocarbon chain alcohol. Such methods, wherein the composition comprises not greater than about 50 wt % of the lower hydrocarbon chain alcohol. Such methods, wherein the composition further comprises a surfactant. Such methods, wherein the composition comprises not greater than about 5 wt % surfactant. Such methods, wherein the composition further comprises humectants, emulsifiers, or combinations thereof. Such methods, wherein the composition is free of a non-polymeric cationic antimicrobial.

EXAMPLES

Objects and advantages are further illustrated by the following examples, but the particular materials and amounts thereof recited in these examples, as well as other conditions and details, should not be construed to unduly limit this disclosure.

Table 1 describes the list of reagents utilized herein.

TABLE 1

| Trade Name | Company | Chemical |
| --- | --- | --- |
| CHG (20% Solids In Water) | Xxtrium Laboratories, Chicago, IL | Chlorhexidine gluconate |
| Cosmocil CQ (20% Solids In Water) | Arch Chemicals, Norwalk, CT | Polyhexamethylene biguanide hydrochloride (PHMB) |
| Tween 20 | Alfa Aesar, Ward Hill, MA | Polysorbate 20 |
| Glycerol Anhydrous Pure | EMD Chemicals, Gibbstown, NJ | glycerol |
| Carrageenan (type II) | Aldrich Chemical Company, Inc., Milwaukee, WI | t-carrageenan |
| Keltrol CG-F | C P Kelco, Atlanta, GA | xanthan gum |
| Alginic Acid | Sigma Chemical Company, St. Louis, MO | alginate |
| 1,000N Hydrochloric Acid | J. T. Baker, Mallinekrodt Baker Inc., Phillipsburg, NJ | HCl |
| 1,000N Sodium Hydroxide | VWR International, West Chester, PA | NaOH |
| Premium Kandiyohi Purified Water | Chippewa Falls, WI PKD 4/13/11 0104 | $H_2O$ |
| Potassium dihydrogen phosphate | Sigma-Aldrich Corp., St. Louis, MO | $KH_2PO_4$ |
| Sodium hydrogen phosphate | Sigma-Aldrich Corp., St. Louis, MO | $Na_2HPO_4$ |
| Triton X-100 | Sigma-Aldrich Corp., St. Louis, MO | 4-(,1,3,3-Tetramethylbutyl)phenyl-polyethylene glycol |

TABLE 1-continued

| Trade Name | Company | Chemical |
| --- | --- | --- |
| Carbopol Ultrez 10 | Lubrizol Advanced Materials, Cleveland, Ohio | Poly(acrylic acid) |
| Jaguar Excel (Guar gum) | Solvay S. A., Brussels, Belgium | 2-hydroxy-3-(trimethylammonium)propyl ether chloride |
| Ethanol | Columbus Chemical Industries, Columbus, WI | $CH_3CH_2OH$ |
| PCMX | Sigma-Aldrich Corp., St. Louis, MO | 4-chloro-3,5-dimethylphenol |
| Irgasan DP300 Triclosan | Novartis, Basel, Switzerland | 5-chloro-2-(2,4-dichlorophenoxy)phenol |
| Dishman JAQ (BKC C-14) | Dishman Pharmaceuticals and Chemicals, Ahmedabad, India | benzalkonium chloride |
| Octenidine dihydrochloride | Dishman Pharmaceuticals and Chemicals, Ahmedabad, India | N,N'-(decane-1,10-diyldipyridin-1-yl-4-ylidene)dioctan-1-amine dihydrochloride |
| Pluronic P65 | BASF, Ludwigshafen, Germany | ethylene oxide and propylene oxide block copolymer |

TABLE 2

| Trade Name | Company | Active Ingredient | Inactive Ingredients |
| --- | --- | --- | --- |
| Bacti stat AE | Ecolab, St. Paul, MN | 0.3% Triclosan | water, potassium cocoate, SD alcohol 40-B, glycerin, cocamidopropyl PG-dimonium chloride phosphate, potassium stearate, tetrasodium EDTA, hydroxyethylcellulose, fragrance, cocamine oxide, methylparaben, tocopheryl acetate, citric acid, isopropyl alcohol, propylparaben, *aloe barbadensis* leaf juice, FDC blue 1, FDC yellow 5 |
| Endure 200 | Ecolab, St. Paul, MN | 1% Triclosan | water, potassium cocoate, propylene glycol, glycerin, potassium stearate, tetrasodium EDTA, hydroxyethylcellulose, boric acid, cocamine oxide, fragrance, isopropyl alcohol, *aloe barbadensis* leaf juice, FD&C green #3, FD&C blue #1, FD&C yellow #5 |
| Endure 400 | Ecolab, St. Paul, MN | 4% chlorhexidine gluconate | cocamide DEA, cocamine oxide, fragrance, gluconic acid*, gluconolactone*, hydroxyethylcellulose, isopropyl alcohol, PEG-75 lanolin, PEG-150 distearate, propylene glycol, quaternium-60, water *contains one or more of these ingredients |
| Endure 420 | Ecolab, St. Paul, MN | 2% chlorhexidine gluconate | cocamide DEA, cocamine oxide, fragrance, gluconic acid*, gluconolactone*, hydroxyethylcellulose, isopropyl alcohol, PEG-75 lanolin, PEG-150 distearate, propylene glycol, quaternium-60, water *contains one or more of these ingredients |
| Medi-Scrub | Ecolab St Paul, MN | 0.6% PCMX | water, potassium cocoate, glycol stearate, potassium stearate, propylene glycol, glycerin, hydroxyethylcellulose, tetrasodium EDTA, isopropyl alcohol, cocamide DEA, boric acid, cocamine oxide, fragrance, PEG-75 lanolin, methylparaben, propylparaben, *aloe barbadensis* leaf juice, D&C red 33 |
| Betadine ® Surgical Scrub | Purdue Products LP, Stamford, CT | Povidone-iodine (7.5%) - equal to 0.75% available iodine | ammonium nonoxynol-4-sulfate, nonoxynol-9, purified water, sodium hydroxide |
| Sage 2% chlorhexidine gluconate cloths | Sage Products, Cary, IL | 2% chlorhexidine gluconate | *aloe vera*, dimethicone, fragrance, glucono-delta-lactone, glycerin, Igepal, polysorbate 20, propylene glycol, water |
| Comfort Bath Cleansing Washcloths | Sage Products, Cary, IL | none | water, methylpropanediol, glycerin, tetrasodium glutamate diacetate, decyl glucoside, phenoxyethanol, polysorbate 20, citric acid, benzoic acid, dehydroacetic acid, ethylhexylglycerin, simethicone, tocopheryl |

TABLE 2-continued

| Trade Name | Company | Active Ingredient | Inactive Ingredients |
|---|---|---|---|
| TENA Ultra Washcloths | SCA Hygiene Products, Stockholm, Sweden | none | acetate, aloe barbadensis leaf, fragrance water, mineral oil, chamomilla recutita flower extract, aloe barbadensis leaf extract, tocopheryl acetate, fragrance, dimethicone PEG-7 cocoate, isopropyl myristate, glyceryl stearate citrate, sodium hydroxymethylgycinate, PEG-4 laurate, iodoproynyl butylcarbamate, citric acid, disodium EDTA |
| Dey-Engley Neutralizing Broth | Sigma-Aldrich Corp. St. Louis, MO | none | casein enzymic hydrolysate, yeast extract, dextrose, sodium thiosulphate, sodium thioglycollate, sodium bisulphite, lecithin, polysorbate 80, bromo cresol purple |

Example 1

Preparation of Formulations

All of the formulations that were tested for their ability to remove spores from Vitro Skin were constructed in the same fashion.

First the correct amount of cationic antimicrobial was added to a known amount of water and the resultant solution was mixed. Next, the relevant amount of thickener was weighed out and added to the aqueous solution while mixing at 5000 rpm for two minutes. Then, the surfactant was added. The solution was mixed again for two minutes at 5000 rpm. Finally the pH was adjusted accordingly with either NaOH or HCl.

Example 2

General Description of In-Vitro Experiment Designed to Evaluate Ability of Test Formulations to Remove Spores from Skin Like Surfaces The in-vitro method was designed to evaluate the removal of microbes from skin using a synthetic skin material from the cosmetic industry, Vitro-skin from IMS inc, Portland ME This method enables rapid screening of formulations for their propensity to promote release of microbes from skin and may be predictive of in-vivo activity.

Materials

The following materials were utilized. C. sporogenes spores ATCC 3584~1.0×10^8 CFU/ml; Triton-X 100 sampling buffer (pH 7.4) Filter Sterilized: 0.4 g KH2PO4, 10.1 g Na2HPO4, 1 g Triton-X 100, and 1 L dH2O; D/E neutralizing broth; Fingers from disposable polyethylene gloves (VWR 32915-268); Sterile dH2O (WFI quality water); 3M AC Petrifilm; and 5 ml Falcon tubes; 1.5 ml EPI Centrifuge tubes; Petri Dishes; Vitro-Skin IMS Inc.; and double-sided tape.

The method included the following. Punched-out specified number of Vitro-Skin samples using the ¾" punch. Attached punch-out Vitro-Skin samples to a Petri-dish or any other sterile flat surface using double-sided tape. Contaminated the Vitro-Skin samples accordingly with 10 μl of spores/spore prep (~1×10^6 CFU/Sample). Used the pipette tip to spread spores over the surface and used a new pipette tip for each sample. Allowed the samples to dry (~40 minutes). Placed three samples directly into separate finger bags containing 3 ml of triton-x 100 sampling solution or D/E neutralizing broth if one of the samples going to be tested contains antimicrobials. Used the "Finger bag collection method" below for each of the three recovery controls.

The Finger bag collection method was carried out as follows. First, a finger bag was cut from disposable gloves.

For the controls: Filled the finger bag with 3 ml of sampling solution. Placed contaminated Vitro-Skin sample into the finger bag containing sampling solution. Massaged finger bag for 1 minute using thumb and index finger. Removed aliquot of fluid from the finger bag and place into an appropriately labeled 1.5 ml centrifuge tube.

For the tested samples: Placed contaminated Vitro-Skin sample into a finger bag containing 3 ml of appropriate test solution. Massage in finger bag for 20 seconds. Removed the Vitro-Skin sample from the finger bag and place into a new finger bag containing 3 ml of sampling solution (Triton x-100 glove juice buffer or D/E neutralizing broth). Collected sample by using the finger bag collection method noted above. Repeat "Placed contaminated vitro-skin sample . . . " to "Collected sample . . . " for each of the test solutions.

For best statistical data each test solution was repeated 3 times. Heat treated appropriately labeled 1.5 ml centrifuge tubes containing aliquots of solution for 20 min at 80 C. Serially diluted samples in butterfield's buffer and plate 10^-1 to 10^-4 dilution on AC Petrifilm. Heat shocked, diluted, and plated spore stock day of experiment. Incubated Petrifilm in an anaerobic chamber at 37 C for 20-24 hours. Counted plates and analyzed data.

Example 3

Effect of the Addition of Antimicrobial

Various cationic antimicrobials were prepared in water at the concentrations specified in Table 3a and Table 3b below. The pH was adjusted in each sample in Tables 3a and 3b to between 6.3 to 6.7 with either NaOH or HCl.

TABLE 3a

| Ex. 3a | PHMB | CHG | Benzalkonium Chloride (BKC) | Octenidine Hydrochloride | Ethanol | Water | Avg log10 Reduction | St Dev |
|---|---|---|---|---|---|---|---|---|
| 3a-1 | 0 | 0 | 0 | 0 | 0 | 100.00 | 0.74 | 0.06 |
| 3a-2 | 0.04 | 0 | 0 | 0 | 0 | 99.96 | 0.92 | 0.05 |
| 3a-3 | 0.2 | 0 | 0 | 0 | 0 | 99.80 | 0.59 | 0.20 |

TABLE 3a-continued

| Ex. 3a | PHMB | CHG | Benzalkonium Chloride (BKC) | Octenidine Hydrochloride | Ethanol | Water | Avg log10 Reduction | St Dev |
|---|---|---|---|---|---|---|---|---|
| 3a-4 | 1 | 0 | 0 | 0 | 0 | 99.00 | 0.71 | 0.21 |
| 3a-5 | 0 | 0.04 | 0 | 0 | 0 | 99.96 | 0.32 | 0.08 |
| 3a-6 | 0 | 0.2 | 0 | 0 | 0 | 99.80 | 0.22 | 0.10 |
| 3a-7 | 0 | 1 | 0 | 0 | 0 | 99.00 | 0.29 | 0.14 |
| 3a-8 | 0 | 0 | 0.04 | 0 | 0 | 99.96 | 0.27 | 0.07 |
| 3a-9 | 0 | 0 | 0.2 | 0 | 0 | 99.80 | 0.15 | 0.15 |
| 3a-10 | 0 | 0 | 1 | 0 | 0 | 99.00 | 0.35 | 0.11 |
| 3a-11 | 0 | 0 | 0 | 0.04 | 0 | 99.96 | 0.37 | 0.14 |
| 3a-12 | 0 | 0 | 0 | 0.2 | 0 | 99.80 | 0.69 | 0.17 |
| 3a-13 | 0 | 0 | 0 | 0 | 70 | 30.00 | 0.23 | 0.05 |
| 3a-14 | 0 | 0 | 0 | 0 | 40 | 60.00 | 0.29 | 0.06 |
| 3a-15 | 0 | 0 | 0 | 0 | 20 | 80.00 | 0.31 | 0.07 |
| Input Control | | | | | | | 0.00 | 0.08 |

Addition of chlorhexidine gluconate and benzalkonium chloride at all concentrations resulted in poor spore removal. Spore removal seemed to be unaffected by PHMB and higher concentration of octinidine. However, lower concentrations of PHMB (0.04%) resulted in the best response for spore removal.

TABLE 3b

| Ex. 3b | Triclosan | PCMX | PHMB | CHG | Pluronic P65 | Water | Average Log10 Reduction | St dev |
|---|---|---|---|---|---|---|---|---|
| 3b-1 | 0.04 | 0 | 0 | 0 | 0.2 | 99.76 | 0.08 | 0.12 |
| 3b-2 | 0.2 | 0 | 0 | 0 | 2 | 97.80 | 0.07 | 0.14 |
| 3b-3 | 1 | 0 | 0 | 0 | 10 | 89.00 | 0.80 | 0.62 |
| 3b-4 | 0 | 0.04 | 0 | 0 | 0.2 | 99.76 | −0.07 | 0.15 |
| 3b-5 | 0 | 0.2 | 0 | 0 | 2 | 97.80 | 0.15 | 0.46 |
| 3b-6 | 0 | 1 | 0 | 0 | 10 | 89.00 | 1.53 | 0.26 |
| 3b-7 | 0 | 0 | 0.04 | 0 | 0.2 | 99.76 | 0.56 | 0.07 |
| 3b-8 | 0 | 0 | 0.2 | 0 | 2 | 97.80 | 0.97 | 0.20 |
| 3b-9 | 0 | 0 | 1 | 0 | 10 | 89.00 | 0.72 | 0.51 |
| 3b-10 | 0 | 0 | 0 | 0.04 | 0.2 | 99.76 | −0.09 | 0.04 |
| 3b-11 | 0 | 0 | 0 | 0.2 | 2 | 97.80 | −0.21 | 0.10 |
| 3b-12 | 0 | 0 | 0 | 1 | 10 | 89.00 | −0.07 | 0.16 |
| 3b-13 | 0 | 0 | 0 | 0 | 0 | 100.00 | 0.64 | 0.28 |
| Recovery Control | | | | | | | 0.33 | 0.11 |
| Input Control | | | | | | | 0.00 | 0.05 |

As seen in Tables 3a and 3b, non-ionic antimicrobials such as Triclosan and PCMX at higher concentrations (1%) have good log reduction of spores.

Example 4

Effect of pH on Spore Removal Using Either CHG or PHMB as Part of the Formulation Various cationic antimicrobials and thickeners were prepared in water at the concentrations specified in Tables 4a and 4b below.

TABLE 4a

| Ex. 4a | PHMB | CHG | Tween 20 | Glycerol | Carra-geenan | Keltrol CG-F | Algenic Acid | Water | Avg log10 Reduction | St Dev | pH |
|---|---|---|---|---|---|---|---|---|---|---|---|
| 4a-1 | 0 | 0 | 0 | 0 | 0 | 0 | 0 | 100 | 0.88 | 0.08 | 6.5 |
| 4a-2 | 0 | 0 | 3 | 5 | 0 | 0 | 0 | 92 | 0.95 | 0.10 | 6.5 |
| 4a-3 | 0 | 0 | 3 | 5 | 0 | 0.5 | 0 | 91.5 | 1.42 | 0.35 | 6.5 |
| 4a-4 | 0.04 | 0 | 3 | 5 | 0 | 0.5 | 0 | 91.46 | 1.23 | 0.31 | 6.5 |
| 4a-5 | 0 | 0 | 3 | 5 | 0.5 | 0 | 0 | 91.5 | 1.39 | 0.44 | 5 |
| 4a-6 | 0 | 0 | 3 | 5 | 0.5 | 0 | 0 | 91.5 | 1.66 | 0.11 | 6 |
| 4a-7 | 0 | 0 | 3 | 5 | 0.5 | 0 | 0 | 91.5 | 0.87 | 0.20 | 7 |

TABLE 4a-continued

| Ex. 4a | PHMB | CHG | Tween 20 | Glycerol | Carra- geenan | Keltrol CG-F | Algenic Acid | Water | Avg log10 Reduction | St Dev | pH |
|---|---|---|---|---|---|---|---|---|---|---|---|
| 4a-8 | 0 | 0 | 3 | 5 | 0.5 | 0 | 0 | 91.5 | 1.62 | 0.08 | 8 |
| 4a-9 | 0 | 0.1 | 3 | 5 | 0.5 | 0 | 0 | 91.4 | 1.99 | 0.15 | 5 |
| 4a-10 | 0 | 0.1 | 3 | 5 | 0.5 | 0 | 0 | 91.4 | 2.02 | 0.06 | 6 |
| 4a-11 | 0 | 0.1 | 3 | 5 | 0.5 | 0 | 0 | 91.4 | 2.03 | 0.04 | 7 |
| 4a-12 | 0 | 0.1 | 3 | 5 | 0.5 | 0 | 0 | 91.4 | 1.80 | 0.15 | 8 |
| 4a-13 | 0 | 0 | 3 | 5 | 0 | 0 | 0.5 | 91.5 | 1.81 | 0.06 | 5 |
| 4a-14 | 0 | 0 | 3 | 5 | 0 | 0 | 0.5 | 91.5 | 1.94 | 0.03 | 6 |
| 4a-15 | 0 | 0 | 3 | 5 | 0 | 0 | 0.5 | 91.5 | 1.80 | 0.08 | 7 |
| 4a-16 | 0 | 0 | 3 | 5 | 0 | 0 | 0.5 | 91.5 | 1.95 | 0.09 | 8 |
| 4a-17 | 0 | 0.1 | 3 | 5 | 0 | 0 | 0.5 | 91.4 | 1.94 | 0.05 | 5 |
| 4a-18 | 0 | 0.1 | 3 | 5 | 0 | 0 | 0.5 | 91.4 | 1.89 | 0.03 | 6 |
| 4a-19 | 0 | 0.1 | 3 | 5 | 0 | 0 | 0.5 | 91.4 | 1.83 | 0.06 | 7 |
| 4a-20 | 0 | 0.1 | 3 | 5 | 0 | 0 | 0.5 | 91.4 | 1.92 | 0.10 | 8 |
| Recovery Control | | | | | | | | | 0.11 | 0.11 | |
| Input Control | | | | | | | | | 0.00 | 0.05 | |

TABLE 4b

| Ex. 4b | PHMB | Tween 20 | Glycerol | Carra- geenan | Keltrol CG-F | Algenic Acid | Water | Avg log10 Reduction | St Dev | pH |
|---|---|---|---|---|---|---|---|---|---|---|
| 4b-1 | 0 | 0 | 0 | 0 | 0 | 0 | 100 | 0.37 | 0.17 | 6.5 |
| 4b-2 | 0 | 3 | 5 | 0 | 0 | 0 | 92 | 0.26 | 0.26 | 6.5 |
| 4h-3 | 0 | 3 | 5 | 0 | 0.5 | 0 | 91.5 | 1.10 | 0.06 | 6.5 |
| 4h-4 | 0.04 | 3 | 5 | 0 | 0.5 | 0 | 91.46 | 1.08 | 0.13 | 6.5 |
| 4b-5 | 0 | 3 | 5 | 0.5 | 0 | 0 | 91.5 | 0.92 | 0.57 | 5 |
| 4h-6 | 0 | 3 | 5 | 0.5 | 0 | 0 | 91.5 | 1.49 | 0.27 | 6 |
| 4h-7 | 0 | 3 | 5 | 0.5 | 0 | 0 | 91.5 | 1.23 | 0.30 | 7 |
| 4h-8 | 0 | 3 | 5 | 0.5 | 0 | 0 | 91.5 | 1.16 | 0.29 | 8 |
| 4h-9 | 0.04 | 3 | 5 | 0.5 | 0 | 0 | 91.46 | 1.92 | 0.16 | 5 |
| 4b-10 | 0.04 | 3 | 5 | 0.5 | 0 | 0 | 91.46 | 1.96 | 0.31 | 6 |
| 4b-11 | 0.04 | 3 | 5 | 0.5 | 0 | 0 | 91.46 | 2.25 | 0.11 | 7 |
| 4b-12 | 0.04 | 3 | 5 | 0.5 | 0 | 0 | 91.46 | 1.92 | 0.23 | 8 |
| 4b-13 | 0 | 3 | 5 | 0 | 0 | 0.5 | 91.5 | 1.71 | 0.20 | 5 |
| 4b-14 | 0 | 3 | 5 | 0 | 0 | 0.5 | 91.5 | 1.80 | 0.13 | 6 |
| 4b-15 | 0 | 3 | 5 | 0 | 0 | 0.5 | 91.5 | 1.84 | 0.24 | 7 |
| 4b-16 | 0 | 3 | 5 | 0 | 0 | 0.5 | 91.5 | 1.79 | 0.06 | 8 |
| 4b-17 | 0.04 | 3 | 5 | 0 | 0 | 0.5 | 91.46 | 2.02 | 0.12 | 5 |
| 4b-18 | 0.04 | 3 | 5 | 0 | 0 | 0.5 | 91.46 | 1.88 | 0.10 | 6 |
| 4b-19 | 0.04 | 3 | 5 | 0 | 0 | 0.5 | 91.46 | 1.85 | 0.07 | 7 |
| 4b-20 | 0.04 | 3 | 5 | 0 | 0 | 0.5 | 91.46 | 1.94 | 0.12 | 8 |
| Recovery Control | | | | | | | | 0.06 | 0.05 | |

Example 5

Spore Removal Performance of Commercial Products for Patient Bathing and Disclosed Formulations Table 5a shows components of control compositions for the sake of comparison and Table 5b shows spore removal performance of commercial products.

TABLE 5a

| Ex 5 | PHMB | Tween 20 | Glycerol | Water |
|---|---|---|---|---|
| 5-1 | 0 | 0 | 0 | 100 |
| 5-2 | 0.2 | 3 | 5 | 91.8 |

TABLE 5b

| | Average Log10 Reduction | Standard Deviation |
|---|---|---|
| 5-1 | 1.11 | 0.37 |
| 5-2 | 2.22 | 0.13 |

TABLE 5b-continued

| | Average Log10 Reduction | Standard Deviation |
|---|---|---|
| Hibiclens | 0.12 | 0.09 |
| Bacti-stat AE | 0.29 | 0.03 |
| Betadine Surgical Scrub | 1.47 | 0.29 |
| Input Control | 0 | 0.05 |

Example 6

Effect of Competitor Soaps on Spore Removal Performance

Competitor products such as Ecolab Bacti stat AE (0.3% Triclosan), Ecolab Endure 200 (1% Triclosan), Ecolab Endure 400 (4% chlorhexidine gluconate), Ecolab Endure 420 (2% chlorhexidine gluconate), Eclolab Medi-scrub (0.6% PCMX), were evaluated against disclosed compositions. Compositions tested are shown in Table 6a and Table 6b shows spore removal results. While CHG by itself showed poor spore removal, the combination of xanthan gum and CHG in the formulation resulted in spore removal equivalent to that of water.

TABLE 6a

| Ex. 6 | PHMB | CHG | Tween 20 | Glycerol | Xanthan Gum | Water |
|---|---|---|---|---|---|---|
| 6-1 | 0 | 0 | 0 | 0 | 0 | 100 |
| 6-2 | 0.2 | 0 | 3 | 5 | 0.5 | 91.3 |
| 6-3 | 0 | 0.2 | 3 | 5 | 0.5 | 91.3 |

TABLE 6b

| | Average Log10 Reduction | Standard Deviation |
|---|---|---|
| 6-1 | 0.78 | 0.15 |
| 6-2 | 1.42 | 0.12 |
| 6-3 | 1.46 | 0.13 |
| Bacti-Stat AE | 0.33 | 0.19 |
| Endure 200 | 0.60 | 0.13 |

TABLE 6b-continued

| | Average Log10 Reduction | Standard Deviation |
|---|---|---|
| Endure 400 | 0.27 | 0.10 |
| MediScrub | 0.07 | 0.08 |
| Endure 420 | 0.20 | 0.07 |
| Input Control | 0.00 | 0.08 |

As seen above, Xanthan gum with either PHMB or CHG has higher log reduction for spore removal as compared to competitor products.

Example 7

Effect of Charge of Thickener and Viscosity

The compositions shown in Table 7, which all included PHMB, were made and spore removal performance thereof were tested.

TABLE 7

| Ex. 7 | PHMB | Tween 20 | Glycerol | Carra-geenan | Keltrol CG-F | Alginic Acid | Jaguar Excel (quat guar) | Water | Avg Log10 Reduction | St dev |
|---|---|---|---|---|---|---|---|---|---|---|
| 7-1 | 0 | 3 | 5 | 0 | 0 | 0 | 0.5 | 91.5 | 0.94 | 0.03 |
| 7-2 | 0.05 | 3 | 5 | 0 | 0 | 0 | 0.5 | 91.45 | 0.74 | 0.17 |
| 7-3 | 2 | 3 | 5 | 0 | 0 | 0 | 0.5 | 89.5 | 1.04 | 0.13 |
| 7-4 | 0 | 3 | 5 | 0 | 0 | 0 | 1 | 91 | 0.26 | 0.08 |
| 7-5 | 0.05 | 3 | 5 | 0 | 0 | 0 | 1 | 90.95 | 0.36 | 0.27 |
| 7-6 | 2 | 3 | 5 | 0 | 0 | 0 | 1 | 89 | 0.39 | 0.08 |
| 7-7 | 0 | 3 | 5 | 0 | 0.5 | 0 | 0 | 91.5 | 1.22 | 0.13 |
| 7-8 | 0.05 | 3 | 5 | 0 | 0.5 | 0 | 0 | 91.45 | 1.34 | 0.09 |
| 7-9 | 0 | 3 | 5 | 0 | 1 | 0 | 0 | 91 | 0.93 | 0.31 |
| 7-10 | 0.05 | 3 | 5 | 0 | 1 | 0 | 0 | 90.95 | 0.56 | 0.15 |
| 7-11 | 0 | 3 | 5 | 0.5 | 0 | 0 | 0 | 91.5 | 1.49 | 0.14 |
| 7-12 | 0.05 | 3 | 5 | 0.5 | 0 | 0 | 0 | 91.45 | 1.96 | 0.09 |
| 7-13 | 0 | 3 | 5 | 1 | 0 | 0 | 0 | 91 | 0.59 | 0.31 |
| 7-14 | 0.05 | 3 | 5 | 1 | 0 | 0 | 0 | 90.95 | 1.40 | 0.10 |
| 7-15 | 0 | 3 | 5 | 0 | 0 | 0.5 | 0 | 91.5 | 1.54 | 0.15 |
| 7-16 | 0.05 | 3 | 5 | 0 | 0 | 0.5 | 0 | 91.45 | 1.92 | 0.07 |
| 7-17 | 0 | 3 | 5 | 0 | 0 | 1 | 0 | 91 | 1.60 | 0.33 |
| 7-18 | 0.05 | 3 | 5 | 0 | 0 | 1 | 0 | 90.95 | 1.51 | 0.11 |
| 7-19 | 0.05 | 3 | 5 | 0 | 0 | 0 | 0 | 91.95 | 0.95 | 0.51 |
| 7-20 | 2 | 3 | 5 | 0 | 0 | 0 | 0 | 90 | 1.49 | 0.16 |
| 7-21 | 0 | 0 | 0 | 0 | 0 | 0 | 0 | 100 | 0.73 | 0.20 |
| 7-22 | 0 | 3 | 5 | 0 | 0 | 0 | 0 | 92 | 1.04 | 0.50 |
| 7-23 | 0.04 | 3 | 5 | 0 | 0.5 | 0 | 0 | 91.46 | 1.64 | 0.18 |
| Recovery Control | | | | | | | | | 0.21 | 0.07 |
| Input Control | | | | | | | | | 0.00 | 0.01 |

As seen from Table 7, the quat guar by itself at 1% with and without PHMB had poor spore removal performance. The anionic thickeners like xanthan gum, alginic acid and carrageenan increased spore removal.

Example 8

Effect of Charge of Thickener and Viscosity

The compositions shown in Table 8, which all included CHG, were made and spore removal performance thereof were tested.

TABLE 8

| Ex 8 | CHG | PHMB | Tween 20 | Glycerol | Carra-geenan | Keltrol CG-F | Alginic Acid | Jaguar Excel (quat guar) | Water | Avg log10 Reduction | St dev |
|---|---|---|---|---|---|---|---|---|---|---|---|
| 8-1 | 0 | 0 | 3 | 5 | 0 | 0 | 0 | 0.5 | 91.5 | 0.65 | 0.07 |
| 8-2 | 1 | 0 | 3 | 5 | 0 | 0 | 0 | 0.5 | 90.5 | 0.34 | 0.44 |

TABLE 8-continued

| Ex 8 | CHG | PHMB | Tween 20 | Glycerol | Carrageenan | Keltrol CG-F | Alginic Acid | Jaguar Excel (quat guar) | Water | Avg log10 Reduction | St dev |
|---|---|---|---|---|---|---|---|---|---|---|---|
| 8-3 | 2 | 0 | 3 | 5 | 0 | 0 | 0 | 0.5 | 89.5 | 0.49 | 0.35 |
| 8-4 | 0 | 0 | 3 | 5 | 0 | 0 | 0 | 1 | 91 | 0.00 | 0.06 |
| 8-5 | 1 | 0 | 3 | 5 | 0 | 0 | 0 | 1 | 90 | 0.01 | 0.06 |
| 8-6 | 2 | 0 | 3 | 5 | 0 | 0 | 0 | 1 | 89 | 0.02 | 0.18 |
| 8-7 | 0 | 0 | 3 | 5 | 0 | 0.5 | 0 | 0 | 91.5 | 1.10 | 0.12 |
| 8-8 | 0.225 | 0 | 3 | 5 | 0 | 0.5 | 0 | 0 | 91.275 | 0.60 | 0.21 |
| 8-9 | 0 | 0 | 3 | 5 | 0 | 1 | 0 | 0 | 91 | 0.77 | 0.09 |
| 8-10 | 0.225 | 0 | 3 | 5 | 0 | 1 | 0 | 0 | 90.775 | 0.18 | 0.13 |
| 8-11 | 0 | 0 | 3 | 5 | 0.5 | 0 | 0 | 0 | 91.5 | 1.39 | 0.14 |
| 8-12 | 0.2 | 0 | 3 | 5 | 0.5 | 0 | 0 | 0 | 91.3 | 1.88 | 0.06 |
| 8-13 | 0 | 0 | 3 | 5 | 1 | 0 | 0 | 0 | 91 | 0.61 | 0.04 |
| 8-14 | 0.2 | 0 | 3 | 5 | 1 | 0 | 0 | 0 | 90.8 | 1.65 | 0.06 |
| 8-15 | 0 | 0 | 3 | 5 | 0 | 0 | 0.5 | 0 | 91.5 | 1.25 | 0.09 |
| 8-16 | 0.2 | 0 | 3 | 5 | 0 | 0 | 0.5 | 0 | 91.3 | 1.94 | 0.32 |
| 8-17 | 0 | 0 | 3 | 5 | 0 | 0 | 1 | 0 | 91 | 1.52 | 0.15 |
| 8-18 | 0.2 | 0 | 3 | 5 | 0 | 0 | 1 | 0 | 90.8 | 1.60 | 0.09 |
| 8-19 | 0 | 0 | 0 | 0 | 0 | 0 | 0 | 0 | 100 | 0.46 | 0.16 |
| 8-20 | 0 | 0 | 3 | 5 | 0 | 0 | 0 | 0 | 92 | 0.46 | 0.17 |
| 8-21 | 0 | 0.04 | 3 | 5 | 0 | 0.5 | 0 | 0 | 91.46 | 0.99 | 0.20 |
| 8-22 | 1 | 0 | 0 | 0 | 0 | 0 | 0 | 0 | 99 | 0.08 | 0.08 |
| 8-23 | 0.225 | 0 | 0 | 0 | 0 | 0 | 0 | 0 | 99.775 | 0.07 | 0.08 |
| 8-24 | 0.2 | 0 | 0 | 0 | 0 | 0 | 0 | 0 | 99.8 | 0.14 | 0.06 |
| 8-25 | 2 | 0 | 0 | 0 | 0 | 0 | 0 | 0 | 98 | 0.60 | 0.10 |
| Recovery Control | | | | | | | | | | 0.00 | 0.05 |
| Input Control | | | | | | | | | | 0.00 | 0.11 |

Quat guar at 1% with or without CHG results in poor spore removal performance. Anionic thickeners such as xanthan gum, carrageenan as well as alginic acid used with CHG result in high spore removal.

Example 9

Effect of Carbopol in Formulation for Removal of Spores

TABLE 9a

| Ex 9a | Carbopol (Ultrez 10) | Algenic Acid | PHMB | Tween 20 | Glycerol | Ethanol | Water | Avg Log10 Reduction | St dev |
|---|---|---|---|---|---|---|---|---|---|
| 9a-1 | 0.15 | 0 | 0.05 | 3 | 5 | 5 | 86.8 | 2.42 | 0.14 |
| 9a-2 | 0.15 | 0 | 0.05 | 3 | 5 | 10 | 81.8 | 2.15 | 0.06 |
| 9a-3 | 0.15 | 0 | 0.05 | 3 | 5 | 20 | 71.8 | 1.92 | 0.14 |
| 9a-4 | 0.15 | 0 | 0.05 | 3 | 5 | 50 | 41.8 | 1.45 | 0.23 |
| 9a-5 | 0.15 | 0 | 0 | 3 | 5 | 5 | 86.85 | 1.82 | 0.12 |
| 9a-6 | 0.15 | 0 | 0 | 3 | 5 | 10 | 81.85 | 1.74 | 0.06 |
| 9a-7 | 0.15 | 0 | 0 | 3 | 5 | 20 | 71.85 | 1.49 | 0.09 |
| 9a-8 | 0.15 | 0 | 0 | 3 | 5 | 50 | 41.85 | 1.07 | 0.07 |
| 9a-9 | 0 | 0 | 0 | 0 | 0 | 5 | 95 | 1.04 | 0.15 |
| 9a-10 | 0 | 0 | 0 | 0 | 0 | 10 | 90 | 0.99 | 0.23 |
| 9a-11 | 0 | 0 | 0 | 0 | 0 | 20 | 80 | 0.92 | 0.08 |
| 9a-12 | 0 | 0 | 0 | 0 | 0 | 35 | 65 | 0.86 | 0.13 |
| 9a-13 | 0.15 | 0 | 0.05 | 3 | 0 | 0 | 96.8 | 1.73 | 0.13 |
| 9a-14 | 0.15 | 0 | 0 | 3 | 5 | 0 | 91.85 | 1.57 | 0.04 |
| 9a-15 | 0 | 0 | 0.05 | 0 | 0 | 0 | 99.95 | 1.11 | 0.20 |
| 9a-16 | 0 | 1 | 0 | 3 | 5 | 0 | 91 | 0.92 | 0.22 |
| 9a-17 | 0 | 1 | 0.05 | 3 | 5 | 0 | 90.95 | 1.22 | 0.18 |
| 9a-18 | 0 | 0 | 0 | 0 | 0 | 0 | 100 | 0.67 | 0.13 |
| Input Control | | | | | | | | −0.02 | 0.03 |
| Recovery Control | | | | | | | | 0.00 | 0.03 |

TABLE 9b

| Ex9b | Carbopol (Ultrez 10) | Alginic Acid | PHMB | Tween 20 | Glycerol | Ethanol | Water | Avg Log10 Reduction | St dev |
|---|---|---|---|---|---|---|---|---|---|
| 9b-1 | 0.15 | 0 | 0.05 | 3 | 5 | 5 | 86.8 | 2.10 | 0.03 |
| 9b-2 | 0.15 | 0 | 0 | 3 | 5 | 5 | 86.85 | 2.14 | 0.14 |
| 9b-3 | 0 | 1 | 0.05 | 3 | 5 | 0 | 90.95 | 1.86 | 0.06 |
| 9b-4 | 0 | 1 | 0 | 3 | 5 | 0 | 91 | 1.26 | 0.38 |
| 9b-5 | 0 | 0 | 0 | 0 | 0 | 5 | 95 | 0.68 | 0.07 |
| 9b-6 | 0 | 0 | 0 | 0 | 0 | 0 | 100 | 0.57 | 0.06 |
| 9b-7 | 0 | 0 | 0 | 3 | 5 | 5 | 87 | 1.34 | 0.06 |
| 9b-8 | 0 | 0 | 0 | 3 | 5 | 0 | 92 | 1.19 | 0.20 |
| Input Control | | | | | | | | −0.05 | 0.03 |
| Recovery Control | | | | | | | | 0.00 | 0.03 |

Thus, embodiments of methods for spore removal are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The invention claimed is:

1. A method for removing spores from skin, the method comprising:
   A) contacting a skin surface with a composition, the composition comprising:
      a) water in an amount not less than 40 wt % by weight of the composition;
      b) a polysorbate surfactant in an amount not less than 0.5 wt % and not greater than 5 wt %;
      c) a polymeric anionic thickener in an amount from about 0.1 wt % to about 4 wt %, the polymeric anionic thickener being selected from the group consisting of carrageenan, alginic acid, xanthan gum, a polyacrylic acid, and a combination thereof; and
      d) a cationic antimicrobial in an amount from about 0.04 wt % to about 4 wt %, the cationic antimicrobial being selected from CHG and PHMB, wherein:
         i) the composition excludes ethanol;
         ii) the composition is free of non-ionic thickener;
         iii) the composition is free of non-cationic antimicrobials; and
         iv) the composition is a solution; and
   B) mechanically acting on the skin surface for at least one (1) second while the skin surface is in the presence of the composition; and
   C) removing at least a portion of the composition from the surface of the skin, wherein spores are removed from the skin surface upon removing the composition, and wherein the composition is effective to remove spores at an average log 10 reduction value that is greater than an average log 10 reduction value for removal of spores with water alone.

2. The method of claim 1, wherein the cationic antimicrobial is present in an amount from about 0.04 wt % to about 0.3 wt %.

3. The method of claim 1, the composition further comprising glycerol present in an amount from about 2 to about 20 wt % with respect to the weight of the composition.

4. The method of claim 1, the composition further comprising glycerol.

5. The method of claim 1, wherein the skin surface is contacted with about 1 mL/10 cm$^2$ of the skin surface.

6. The method of claim 1, wherein the removing of the composition from the skin surface is accomplished without addition of water.

7. The method of claim 4, the composition comprising glycerol present in an amount of 5 wt % with respect to the weight of the composition.

8. The method of claim 1, wherein the polysorbate surfactant is polysorbate 20.

9. The method of claim 1, wherein the polysorbate surfactant is present in an amount of 3 wt % with respect to the weight of the composition.

10. The method of claim 1, wherein the cationic antimicrobial is PHMB present in an amount of 0.05 wt % with respect to the weight of the composition.

11. The method of claim 1, wherein the cationic antimicrobial is CHG present in an amount of 0.2 wt % with respect to the weight of the composition.

12. The method of claim 1, the composition comprising carrageenan present in an amount of 0.5 wt % with respect to the weight of the composition.

13. The method of claim 1, the composition comprising alginic acid present in an amount of 0.5 wt % with respect to the weight of the composition.

14. The method of claim 1, the composition comprising a polyacrylic acid present in an amount of 0.15 wt % with respect to the weight of the composition.

15. The method of claim 1, wherein water is present in an amount from 70 wt % to 99 wt % with respect to the weight of the composition.

* * * * *